United States Patent
Markosyan et al.

(10) Patent No.: US 11,969,001 B2
(45) Date of Patent: *Apr. 30, 2024

(54) **FOOD INGREDIENTS FROM *STEVIA REBAUDIANA***

(71) Applicant: PureCircle USA Inc., Chicago, IL (US)

(72) Inventors: Avetik Markosyan, Yerevan (AM); Yeen Yee Wong, Kuala Lumpur (MY); Pei Chen Koh, Klang (MY)

(73) Assignee: PURECIRCLE USA INC., Westchester, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/005,096

(22) Filed: Aug. 27, 2020

(65) Prior Publication Data

US 2020/0390135 A1 Dec. 17, 2020

Related U.S. Application Data

(63) Continuation-in-part of application No. 16/700,954, filed on Dec. 2, 2019, now Pat. No. 11,439,169, which is a continuation of application No. 15/887,052, filed on Feb. 2, 2018, now Pat. No. 10,492,516, which is a continuation-in-part of application No. PCT/US2017/063765, filed on Nov. 29, 2017.

(60) Provisional application No. 62/892,286, filed on Aug. 27, 2019, provisional application No. 62/427,539, filed on Nov. 29, 2016.

(51) Int. Cl.

| | |
|---|---|
| *A23L 2/60* | (2006.01) |
| *A23G 1/48* | (2006.01) |
| *A23L 27/30* | (2016.01) |
| *A24B 13/00* | (2006.01) |
| *A24B 15/40* | (2006.01) |
| *A61K 8/60* | (2006.01) |
| *A61K 9/00* | (2006.01) |
| *A61K 9/08* | (2006.01) |
| *A61K 47/26* | (2006.01) |
| *A61K 47/46* | (2006.01) |
| *A61Q 11/00* | (2006.01) |
| *A61Q 19/00* | (2006.01) |
| *C07H 1/08* | (2006.01) |
| *C07H 15/24* | (2006.01) |

(52) U.S. Cl.
CPC .............. *A23L 27/34* (2016.08); *A23G 1/48* (2013.01); *A23L 2/60* (2013.01); *A23L 27/33* (2016.08); *A23L 27/36* (2016.08); *A24B 13/00* (2013.01); *A24B 15/403* (2013.01); *A61K 8/602* (2013.01); *A61K 9/0095* (2013.01); *A61K 9/08* (2013.01); *A61K 47/26* (2013.01); *A61K 47/46* (2013.01); *A61Q 19/00* (2013.01); *C07H 1/08* (2013.01); *C07H 15/24* (2013.01); *A23V 2002/00* (2013.01); *A61K 2800/10* (2013.01); *A61Q 11/00* (2013.01)

(58) Field of Classification Search
CPC .......... A23L 27/34; A23L 27/36; A23L 27/33; A24B 13/00; A24B 15/403; C07H 15/24; C07H 1/08; A61Q 19/00; A61Q 11/00; A61K 8/602; A61K 47/46; A61K 9/08; A61K 9/0095; A61K 47/26; A61K 2800/10; A23V 2002/00
See application file for complete search history.

(56) References Cited

U.S. PATENT DOCUMENTS

| | | | |
|---|---|---|---|
| 4,599,403 A | 7/1986 | Kumar | |
| 7,923,541 B2 | 4/2011 | Yang | |
| 8,197,875 B2 | 6/2012 | Chien et al. | |
| 8,420,141 B2 | 4/2013 | Roy et al. | |
| 9,029,426 B2* | 5/2015 | Markosyan | A61K 47/26 514/777 |
| 9,901,110 B2* | 2/2018 | Markosyan | A61Q 19/00 |
| 2005/0129827 A1 | 6/2005 | Miljkovic et al. | |
| 2009/0017185 A1 | 1/2009 | Catani | |
| 2009/0130285 A1 | 5/2009 | Abraham et al. | |
| 2010/0112159 A1 | 5/2010 | Abelyan | |
| 2010/0227034 A1 | 9/2010 | Purkayastha et al. | |
| 2011/0124587 A1 | 5/2011 | Jackson et al. | |
| 2012/0189750 A1 | 7/2012 | Chien et al. | |
| 2013/0071339 A1* | 3/2013 | Markosyan | A23L 2/60 514/777 |
| 2013/0303633 A1 | 11/2013 | Markosyan | |
| 2018/0168212 A1 | 6/2018 | Markosyan et al. | |
| 2019/0223481 A1 | 7/2019 | Gaspard et al. | |

FOREIGN PATENT DOCUMENTS

| | | |
|---|---|---|
| CN | 102617667 A | 8/2012 |
| CN | 105001281 A | 10/2015 |
| JP | 2904974 | 6/1999 |
| JP | 2013230159 A | 3/2016 |

(Continued)

OTHER PUBLICATIONS

Gawel-Beben, Katarzyna et al., "Stevia Rebaudiana Bert. Leaf Extracts as a Multifunctional Source of Natural Antioxidants", Published in Molecules; vol. 20, pp. 5468-5486; Mar. 27, 2015.
International Search Report and Written Opinion of PCT/US2017/063765.

(Continued)

*Primary Examiner* — Shirley V Gembeh

(57) ABSTRACT

The invention relates to a process for producing food ingredients from *Stevia rebaudiana* plant and their use in food products, beverages and other consumables. Obtained compositions are useful as flavors, sweeteners, antioxidants, and other functional ingredients.

6 Claims, 2 Drawing Sheets

(56) References Cited

FOREIGN PATENT DOCUMENTS

| RU | 2239333 C1 | 11/2004 |
|---|---|---|
| RU | 2380989 C2 | 2/2010 |
| WO | 02/100192 A1 | 12/2002 |
| WO | 2007061795 A1 | 5/2007 |
| WO | 2018/102447 | 6/2018 |

OTHER PUBLICATIONS

Katarzyna Gawel-Beben et al, "Stevia Rebaudiana Bert. Leaf Extracts as a Multifunctional Source of Natural Antioxidants", Molecules, (Mar. 27, 2015), vol. 20, No. 4, doi: 10.3390/molecules20045468, pp. 5468-5486, XP055667897 [X] 1-4.

* cited by examiner

FOOD INGREDIENTS FROM *STEVIA REBAUDIANA*

RELATED APPLICATIONS

This application claims the benefit of U.S. Provisional Application No. 62/892,286, filed Aug. 27, 2019, which is incorporated by reference herein in its entirety. This application is also a continuation-in-part of U.S. application Ser. No. 16/700,954, filed Dec. 2, 2019, which is a continuation of U.S. application Ser. No. 15/887,052, filed Feb. 2, 2018, now granted as U.S. Pat. No. 10,492,516, which is a continuation-in-part of International Patent Application No. PCT/US2017/063765, filed Nov. 29, 2017, which claims priority to U.S. Patent Application No. 62/427,539, filed Nov. 29, 2016, each of which applications is incorporated by reference herein in its entirety.

This application also incorporates by reference each of the following applications in its entirety: U.S. patent application Ser. No. 16/539,730, filed on Aug. 13, 2019, published as US 2019/0364944; U.S. patent application Ser. No. 15/905,414, filed on Feb. 26, 2018, now granted as U.S. Pat. No. 10,420,359; U.S. patent application Ser. No. 15/284,265, filed on Oct. 3, 2016, now granted as U.S. Pat. No. 9,901,110; U.S. patent application Ser. No. 14/677,538, filed on Apr. 2, 2015, now granted as U.S. Pat. No. 9,456,626; U.S. patent application Ser. No. 13/993,415, filed on Jun. 12, 2013, now granted as U.S. Pat. No. 9,029,426; International Application No. PCT/US2011/064343, filed on Dec. 12, 2011, published as WO 2012/082587; U.S. Patent Application No. 61/424,798, filed on Dec. 20, 2010; U.S. Patent Application No. 61/422,403, filed on Dec. 13, 2010; U.S. patent application Ser. No. 13/530,113, filed on Jun. 22, 2012, now granted as U.S. Pat. No. 8,530,527; U.S. patent application Ser. No. 13/580,098, filed on Nov. 6, 2012, now granted as U.S. Pat. No. 8,981,081; U.S. patent application Ser. No. 13/943,776, filed on Jul. 16, 2013, published as US 2013/0303633; U.S. patent application Ser. No. 13/957,098, filed on Aug. 1, 2013, now granted as U.S. Pat. No. 9,510,611; U.S. patent application Ser. No. 14/195,812, filed on Mar. 3, 2014, published as US 2015/0044357; and U.S. patent application Ser. No. 14/829,127, filed on Aug. 18, 2015, now granted as U.S. Pat. No. 9,771,434.

FIELD OF THE INVENTION

The invention relates to a process for producing food ingredients from *Stevia rebaudiana* plant and their use in food products, beverages and other consumables.

DESCRIPTION OF THE RELATED ART

High intensity sweeteners possess a sweetness level many times exceeding that of sucrose. They are essentially non-caloric and used widely in manufacturing of diet and reduced calorie food. Although natural caloric sweeteners such as sucrose, fructose, and glucose provide the most desirable taste to consumers, they possess high calorie values. High intensity sweeteners do not affect the blood glucose level and provide little or no nutritive value.

*Stevia rebaudiana* Bertoni is a perennial shrub of the Asteraceae (Compositae) family native to certain regions of South America. The leaves of the plant contain from 10 to 20% of diterpene glycosides, which are around 150 to 450 times sweeter than sugar. The leaves have been traditionally used for hundreds of years in Paraguay and Brazil to sweeten local teas and medicines.

At present, there are more than 230 *Stevia* species with significant sweetening properties. The plant has been successfully grown under a wide range of conditions from its native subtropics to the cold northern latitudes.

The extract of *Stevia rebaudiana* plant contains a mixture of different sweet diterpene glycosides, which have a single base—steviol—and differ by the presence of carbohydrate residues at positions C13 and C19. These glycosides accumulate in *Stevia* leaves and compose approximately 10%-20% of the total dry weight. Typically, on a dry weight basis, the four major glycosides found in the leaves of *Stevia* are Dulcoside A (0.3%), Rebaudioside C (0.6-1.0%), Rebaudioside A (3.8%) and Stevioside (9.1%). Other glycosides identified in *Stevia* extract include Rebaudioside B, C, D, E, and F, Steviolbioside and Rubusoside.

Steviol glycosides have zero calories and can be used wherever sugar is used. They are ideal for diabetic and low-calorie diets.

On the other hand, it has to be noted that in process of manufacture along with steviol glycosides large amounts of other constituents of *Stevia* plant are also extracted with water. These other constituents are mainly separated during downstream processing and discarded into environment.

Little is known about these other constituents of *Stevia rebaudiana* plant. Few authors reported phenolics compounds, free amino acids etc. however the information about the identity of those constituents remains scarce and their possible uses in foods, beverages and other consumables is not described (Karakose, et al, 2011, 2015; Wölwer-Rieck, 2012; Periche et al, 2014).

There is no reports to-date on processing the other extracted constituents of *Stevia* plant into any food ingredient. So, if accomplished in large scale, this can provide significant economic, and environmental benefits as it can provide an opportunity for inclusion of whole stevia plant into food chain, creating practically wasteless stevia processing.

Therefore, there's a need to develop a method to effectively isolate those constituents form the *Stevia rebaudiana* plant and use them as ingredients in different consumables.

SUMMARY OF THE INVENTION

The present invention is aimed to overcome the disadvantages of existing *Stevia* industrial processing schemes. The invention describes a process for producing food ingredients from the *Stevia rebaudiana* plant and use thereof in various consumables including food products and beverages.

The invention, in part, pertains to compositions comprising phenolics and other non-steviol glycoside compounds, derived from *Stevia rebaudiana* plant.

Hereinafter the term "steviol glycoside(s)" will mean steviol glycosides naturally occurring in *Stevia rebaudiana*, including but not limited to steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside D, rebaudioside N, rebaudioside O, and combinations thereof.

Hereinafter the terms "RebA", "RebB", "RebC", "RebD", "RebE", "RebF", "RebM", "RebN", and "RebO" refer to Rebaudiosides A, B, C, D, E, F, M, N, and O.

Hereinafter the terms "Stev", "Sbio", "DulA", "Rub", refer to Stevioside, Steviolbioside, Dulcoside A and Rubusoside.

Hereinafter the term "TSG content" will mean Total Steviol Glycosides (TSG) content, and it will be calculated as the sum of the concentrations of Rebaudioside A, Rebaudioside B, Rebaudioside C, Rebaudioside D, Rebaudioside E, Rebaudioside F, Rebaudioside M, Rebaudioside N, Rebaudioside O, Stevioside, Steviolbioside, Dulcoside A and Rubusoside on a wt/wt dry basis.

Hereinafter the term "CGA(s)" will mean chlorogenic acids and their derivatives naturally occurring in plants, including but not limited to neo-chlorogenic acid (neo-CGA; 5-O-caffeoylquinic acid or 5-CQA), crypto-chlorogenic acid (crypto-CGA; 4-O-caffeoylquinic acid or 4-CQA), n-chlorogenic acid (n-CGA; 3-O-caffeoylquinic acid or 3-CQA), iso-chlorogenic acid A (iso-CGA A; 3,5-dicaffeoylquinic acid) iso-chlorogenic acid B (iso-CGA B; 3,4-dicaffeoylquinic acid), iso-chlorogenic acid C (iso-CGA C; 4,5-dicaffeoylquinic acid), and combinations thereof.

Hereinafter the term "TCGA content" will mean Total Chlorogenic Acids (TCGA) content, and it will be calculated as the sum of the concentrations of neo-CGA, crypto-CGA, n-CGA, iso-CGA A, iso-CGA B, and iso-CGA C on a wt/wt dry basis.

In the invention, Stevia rebaudiana plant material, particularly the leaves and/or stems, were used as a starting material.

The plant material was subjected to extraction using water or aqueous alcohol solvent.

The obtained water or aqueous alcohol extract was further processed to separate steviol glycosides fraction. The remaining fraction was designated as "non-steviol glycoside composition" (NSGC)—meaning a composition predominately comprising compounds, other than steviol glycosides, which occur in the water or aqueous alcohol extracts of Stevia rebaudiana plant (hereinafter "non-steviol glycoside molecules"). Not limiting examples of "non-steviol glycoside molecules" include phenolic compounds, polyphenols, flavonoids, quinic and caffeic acids and their derivatives, neo-chlorogenic acid (neo-CGA; 5-O-caffeoylquinic acid or 5-CQA), crypto-chlorogenic acid (crypto-CGA; 4-O-caffeoylquinic acid or 4-CQA), n-chlorogenic acid (n-CGA; 3-O-caffeoylquinic acid or 3-CQA), iso-chlorogenic acid A (iso-CGA A; 3,5-dicaffeoylquinic acid) iso-chlorogenic acid B (iso-CGA B; 3,4-dicaffeoylquinic acid), iso-chlorogenic acid C (iso-CGA C; 4,5-dicaffeoylquinic acid), other chlorogenic acids and iso-chlorogenic acids known to art, retinoids, pigments, polysaccharides, olygosaccharides, disaccharides, monosaccharides, volatile oil components, sterols, terpenoids, sesquiterpenoids, diterpenes, triterpenes, coumarins, fatty acids and their derivatives, amino acids and their derivatives, dipeptides, oligopeptides, polypeptides, proteins, austroinulin, quercetin, sterebins, spathulenol, decanoic acid, 8,11,14-ecosatrienoic acid, 2-methyloctadecane, pentacosane, octacosane, stigmasterol, bsitosterol, a- and b-amyrine, lupeol, b-amyrin acetate, pentacyclic triterpene and/or glycosides thereof.

The compositions prepared in some embodiments of present invention and designated as NSGC may also contain some residual amounts of steviol glycosides.

Some NSGCs may be further purified and/or otherwise processed by any food ingredient processing method known to art to obtain other NSGCs.

NSGCs of present invention are applicable in various consumables, foods and beverages as, flavors, flavor modifiers, flavor enhancers, sweeteners, preservatives, antioxidants, emulsifiers, texturizing, bulking, stabilizing, solubilizing agents and other food ingredients.

It is to be understood that both the foregoing general description and the following detailed description are exemplary and explanatory and are intended to provide further explanation of the invention as claimed.

BRIEF DESCRIPTION OF THE DRAWINGS

The accompanying drawing is included to provide a further understanding of the invention. The drawing illustrates embodiments of the invention and together with the description serve to explain the principles of the embodiments of the invention.

DETAILED DESCRIPTION OF THE INVENTION

Figure 1:
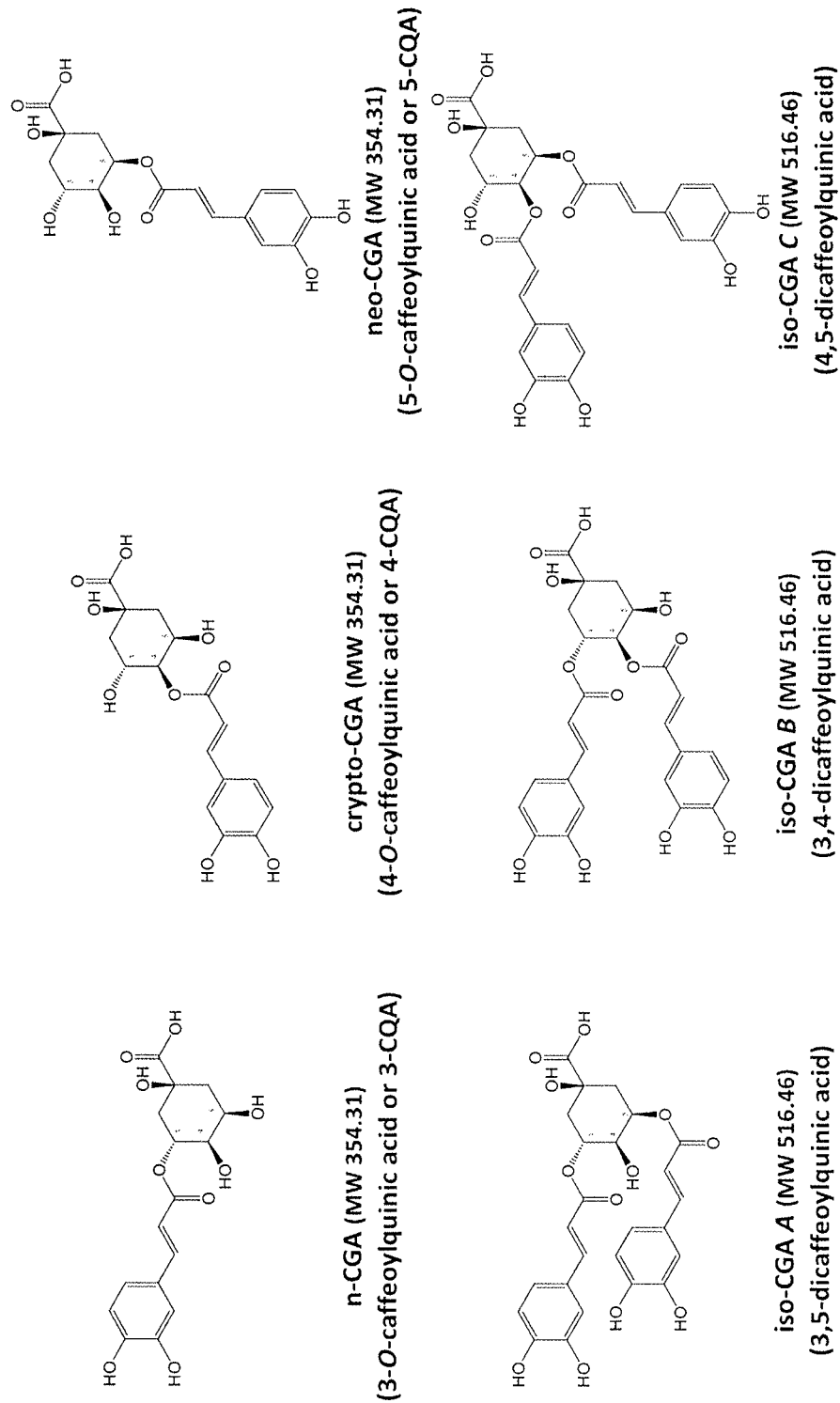
FIG. 1 shows the structures of some CGAs.
Figure 2:
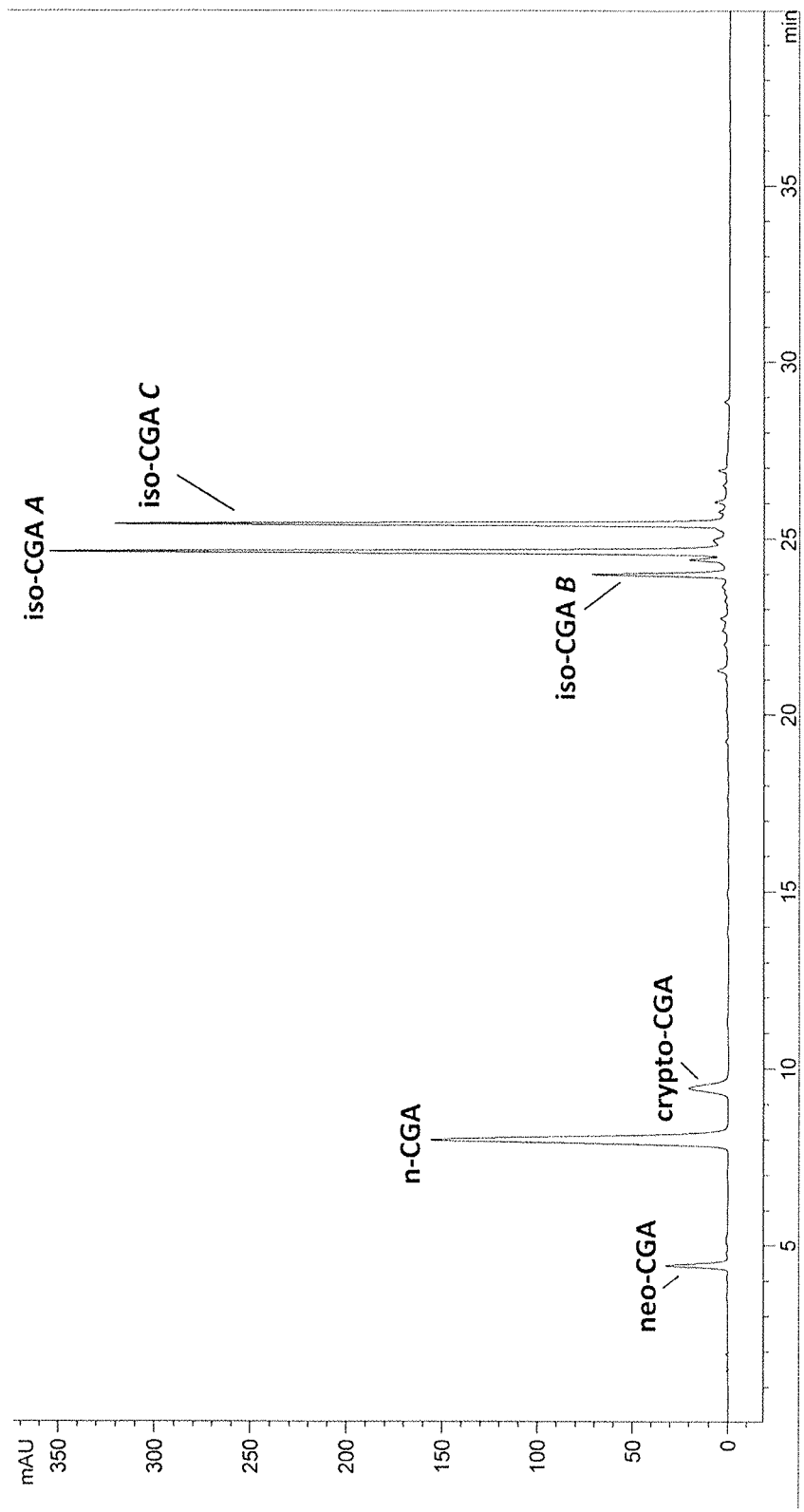
FIG. 2 shows the HPLC chromatogram of Stevia rebaudiana CGA.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Those of skill in the art will also recognize that one or more of the further process steps described below, may be omitted. Those experienced in art will also understand that although the process described below assumes certain order of the described steps, this order can be altered in some cases.

Extraction

In the invention, Stevia rebaudiana plant material, particularly the leaves and/or stems of Stevia rebaudiana plant, were used as a starting material. The Stevia rebaudiana plant material extract can be obtained using any method such as, but not limited to, the extraction methods described in U.S. Pat. No. 7,862,845, the entire contents of which are incorporated by reference herein, as well as membrane filtration, supercritical fluid extraction, enzyme-assisted extraction, microorganism-assisted extraction, ultrasound-assisted extraction, microwave-assisted extraction, etc.

In one embodiment, the Stevia rebaudiana plant material (e.g. leaves) may be dried at temperatures between about 20° C. to about 100° C. until moisture content between about 5% and about 15% is reached. In a particular embodiment, the plant material may be dried between about 20° C. and about 60° C. for a period of time from about 1 to about 240 hours, In other particular embodiments, the plant material may be dried at temperatures between about 20° C. to about 35° C. to prevent decomposition.

In some embodiments, the Stevia rebaudiana plant material may be dried under vacuum or reduced pressure.

In some embodiments, the Stevia rebaudiana plant material may be dried in the presence of inert gas such as $N_2$.

In some embodiments, the Stevia rebaudiana plant material may be freeze dried.

In some embodiments, the dried plant material is optionally milled. Particle sizes may be between about 0.1 to about 20 mm.

The plant material (milled or unmilled) may be extracted by any suitable extraction process, such as, for example, continuous or batch reflux extraction, supercritical fluid extraction, enzyme-assisted extraction, microorganism-assisted extraction, ultrasound-assisted extraction, microwave-assisted extraction, etc. The solvent used for the extraction can be any suitable solvent, such as for example, polar organic solvents (degassed, vacuumed, pressurized or distilled), non-polar organic solvents, water (degassed, vacuumed, pressurized, deionized, distilled, carbon-treated or reverse osmosis) or a mixture thereof. In a particular embodiment, the solvent comprises water and one or more alcohols. In another embodiment, the solvent is water. In another embodiment, the solvent is one or more alcohols. The alcohol can be selected from, for example, methanol, ethanol, n-propanol, 2-propanol, 1 butanol, 2-butanol and mixtures thereof.

In a particular embodiment, the plant material is extracted with water in a continuous reflux extractor. One of skill in the art will recognize the ratio of extraction solvent to plant material will vary based on the identity of the solvent and the amount of plant material to be extracted. Generally, the ratio of extraction solvent to kilogram of dry plant material is from about 20 liters to about 25 liters to about one kilogram of leaves.

The pH of the extraction solvent can be between about pH 2.0 and 7.0, such as, for example, between about pH 2.0 and about pH 5.0, between about pH 2.0 and about pH 4.0 or between about pH 2.0 and about pH 3.0. In a particular embodiment, the extraction solvent is aqueous, e.g. water and, optionally, acid and/or base in an amount to provide a pH between about pH 2.0 and 7.0, such as, for example, between about pH 2.0 and about pH 5.0, between about pH 2.0 and about pH 4.0 or between about pH 2.0 and about pH 3.0. Any suitable acid or base can be used to provide the desired pH for the extraction solvent, such as, for example, HCl, NaOH, citric acid, and the like.

The extraction may be carried out at temperatures between about 25° C. and about 100° C., such as, for example, between about 30° C. and about 80° C., between about 35° C. and about 75° C., between about 40° C. and about 70° C., between about 45° C. and about 65° C. or between about 50° C. and about 60° C.

In embodiments where the extraction process is a batch extraction process, the duration of extraction may range from about 0.5 hours to about 24 hours, such as, for example, from about 1 hour to about 12 hours, from about 1 hour to about 8 hours, or from about 1 hour to about 6 hours.

In embodiments where the extraction process is a continuous process, the duration of extraction may range from about 1 hour to about 5 hours, such as, for example, from about 2.5 hours to about 3 hours.

After extraction, the insoluble plant material may be separated from the solution by filtration to provide a filtrate containing steviol glycosides and other molecules, described above as "non-steviol glycoside molecules". This solid-liquid separation can be achieved by any suitable means including, but not limited to, gravity filtration, a plate-and-frame filter press, cross flow filters, screen filters, Nutsche filters, belt filters, ceramic filters, membrane filters, microfilters, nanofilters, ultrafilters or centrifugation. Optionally various filtration aids such as diatomaceous earth, bentonite, zeolite etc, may also be used in this process.

Pre-Treatment of Filtrate Containing Steviol Glycosides and "Non-Steviol Glycoside Molecules"

In some embodiments, the filtrate containing steviol glycosides and "non-steviol glycoside molecules" is optionally pre-treated before contacting with macroporous polymeric adsorbent. Said pre-treatment can be achieved for example by at least one agent selected from the group including but not limited to diatomaceous earth, diatomite, kieselgur/kieselguhr, Celite®, bentonite, activated carbon, any food grade filtration aids any flocculation agent, any chelating agent, any acid, any base/alkali, any ion-exchange resin known to art, or combinations thereof. In some embodiments, the pre-treatment can be achieved by additional filtration through ultrafiltration and/or nanofitration and/or RO-filtration membrane systems known to art.

Adsorption of the steviol glycosides

In certain embodiments, the filtrate containing steviol glycosides and "non-steviol glycoside molecules" is contacted with macroporous polymeric adsorbent. The macroporous polymeric adsorbent may be any neutral, acidic, or alkaline macroporous polymeric adsorption resins capable of adsorbing steviol glycosides, such as, for example, the Amberlite® XAD series (Rohm and Haas), Diaion® HP series (Mitsubishi Chemical Corp), Sepabeads® SP series (Mitsubishi Chemical Corp), Cangzhou Yuanwei YWD series (Cangzhou Yuanwei Chemical Co. Ltd., China), or the equivalent. The adsorbent may be packed into columns up to from about 75% to about 100% of their total volume.

Steviol glycosides and some "non-steviol glycoside molecules" are adsorbed by macroporous polymeric adsorbent while other "non-steviol glycoside molecules" are not adsorbed and pass through the column in flow-through effluent.

The macroporous adsorption resin may be eluted by varying concentrations of aqueous Ethanol to obtain various eluate fractions enriched in steviol glycosides and/or "non-steviol glycoside molecules".

In some embodiments, the macroporous adsorption resin may be eluted by varying pH of eluting solvent.

Optional Precipitation of Impurities

The pH of the filtrate containing steviol glycosides and/or "non-steviol glycoside molecules", may be adjusted to remove additional impurities. In one embodiment, the pH of the filtrate can be adjusted to between about 8.5 and about 10.0 by treatment with a base, such as, for example, calcium oxide or hydroxide (about 1.0% from the volume of filtrate) with slow agitation.

Treatment of the filtrate with the base, as set forth above, results in a suspension, the pH of which can be adjusted to about 3.0 to about 4.0 by treatment with any suitable flocculation/coagulation agent. Suitable flocculation/coagulation agents include, for example, potassium alum, aluminum sulfate, aluminum hydroxide, aluminum oxide, $CO_2$, $H_3PO_4$, $P_2O_5$, MgO, $SO_2$, anionic polyacrylamides, quaternary ammonium compounds with long-chain fatty acid substitutents, bentonite, diatomaceous earth, KemTab Sep series, Superfloc series, KemTab Flote series, Kemtalo Mel series, Midland PCS-3000, Magnafloc LT-26, Zuclar 100, Prastal 2935, Talofloc, Magox, iron salts or a combination thereof. Exemplary iron salts include, but are not limited to, $FeSO_4$, $FeCl_2$, $Fe(NO_3)_3$, $Fe_2(SO_4)_3$, $FeCl_3$ and combinations thereof. In a particular embodiment, the ferric salt is $FeCl_3$. The filtrate may be treated with the flocculation/coagulation agent for a duration of time between about 5 minutes to about 1 hour, such as, for example, from about 5 minutes to about 30 minutes, from about 10 minutes to about 20 minutes or from about 10 minutes to about 15 minutes.

Stirred or slow agitation can also be used to facilitate treatment. Optionally, the pH of resultant mixture may then be adjusted to between about 8.5 and about 9.0 with a base, such as, for example, calcium oxide or sodium hydroxide. The duration of time for treatment with base, and optionally, with agitation, is between about 5 minutes to about 1 hour, such as, for example, from about 10 minutes to about 50 minutes, from about 15 minutes to about 45 minutes, from about 20 minutes to about 40 minutes or from about 25 minutes to about 35 minutes. In a particular embodiment, the base is calcium oxide used for a between about 15 and about 40 minutes with slow agitation.

In one embodiment, the filtrate containing steviol glycosides and/or "non-steviol glycoside molecules", may be mixed with at least one alcohol to precipitate some impurities.

Precipitated compounds and insoluble particles are separated from the filtrate to provide composition comprising "non-steviol glycoside molecules". Precipitate separation can be achieved by any suitable means including, but not limited to, gravity filtration, a plate-and-frame filter press, cross flow filters, screen filters, Nutsche filters, belt filters, ceramic filters, membrane filters, microfilters, nanofilters, ultrafilters or centrifugation. Optionally various filtration aids such as diatomaceous earth, bentonite, zeolite etc, may be used in this process.

Deionization

The filtrate containing steviol glycosides and/or "non-steviol glycoside molecules" may be subjected to deionization by any suitable method including, for example, electrodialysis, filtration (nano- or ultra-filtration), reverse osmosis, ion exchange, mixed bed ion exchange or a combination of such methods. In one embodiment, the filtrate containing "non-steviol glycoside molecules" is deionized by treatment with one or more ion exchange resins to provide a resin-treated filtrate. In one embodiment, the filtrate containing steviol glycosides and/or "non-steviol glycoside molecules" is passed through a strong acid cation exchange resin. In another embodiment, the filtrate containing steviol glycosides and/or "non-steviol glycoside molecules" is passed through a weak base anion-exchange resin. In still another embodiment, the filtrate containing steviol glycosides and/or "non-steviol glycoside molecules" is passed through a strong acid cation-exchange resin followed by a weak base anion-exchange resin. In yet another embodiment, the filtrate containing steviol glycosides and/or "non-steviol glycoside molecules" is passed through a weak base anion-exchange resin followed by a strong acid cation-exchange resin.

The cation-exchange resin can be any strong acid cation-exchanger where the functional group is, for example, sulfonic acid. Suitable strong acid cation-exchange resins are known in the art and include, but are not limited to, Rohm & Haas Amberlite® 10 FPC22H resin, which is a sulfonated divinyl benzene styrene copolymer, Dowex® ion exchange resins available from Dow Chemical Company, 15 Serdolit® ion exchange resins available from Serva Electrophoresis GmbH, T42 strong acidic cation exchange resin and A23 strong base an ion exchange resin available from Qualichem, Inc., and Lewatit strong ion exchange resins available from Lanxess. In a particular embodiment, the strong acid cation-exchange resin is Amberlite® 10 FPC22H resin (H+). As would be known to those skilled in the art, other suitable strong acid cation-exchange resins for use with embodiments of this invention are commercially available.

The anion-exchange resin can be any weak base anion-exchanger where the functional group is, for example, a tertiary amine. Suitable weak base anion exchange resins are known in the art and include, but are not limited to, resins such as Amberlite-FPA53 (OH−), Amberlite IRA-67, Amberlite IRA-95, Dowex 67, Dowex 77 and Diaion WA 30 may be used. In a particular embodiment, the strong acid cation-exchange resin is Amberlite-FPA53 (OH−) resin. As would be known to those skilled in the art, other suitable weak base anion-exchange resins for use with embodiments of this invention are commercially available.

In a particular embodiment, the filtrate containing steviol glycosides and/or "non-steviol glycoside molecules" is passed through a strong acid cation-exchange resin, e.g. Amberlite® 10 FPC22H resin (H+), followed by a weak base anion-exchange resin, e.g. Amberlite-FPA53 (OH−), to provide a resin-treated filtrate. The specific velocity (SV) through one or more of the ion exchange columns can be between about 0.01 to about 5 hour −1, such as, for example between about 0.05 to about 4 hour −1, between about 1 and about 3 hour −1 or between about 2 and about 3 hour −1. In a particular embodiment, the specific velocity through the one or more ion exchange columns is about 0.8 hour −1. Following completion of passing the second filtrate containing steviol glycosides through one or more ion exchange columns, the one or more ion exchange columns are washed with water, preferably reverse osmosis (RO) water. The solution obtained from the water wash and the resin-treated filtrate may be combined before proceeding to the multi-column step.

Decolorizing

Decolorization of filtrate containing steviol glycosides and/or "non-steviol glycoside molecules" can be achieved with any known method, such as, for example, contact with activated carbon. The quantity of the activated carbon can be from about 0.1% (wt/vol) to about 0.8% (wt/vol). In a particular embodiment, the quantity of activated carbon is from about 0.25% (wt/vol) to about 0.30% (wt/vol). The suspension may be continuously agitated. The temperature of the treatment can be between about 20° C. and about 30° C., such as, for example, about 25° C. The treatment can be for any duration sufficient to decolorize the eluted solution, such as, for example, between about 20 minutes and about 3 hours, between 20 minutes and about 2 hours, between about 30 minutes and 1.5 hours or between about 1 hour and about 1.5 hours. Following treatment, separation of used carbon can be conducted by any known separation means, such as, for example, gravity or suction filtration, centrifugation or plate-and-frame press filter.

Alternatively, the filtrate containing steviol glycosides and/or "non-steviol glycoside molecules" can be passed through the column packed with activated carbon.

It is to be understood also that treatment with carbon or other decolorizing agent may result not only in decolorizing effect but also provide improvement of taste, flavor, aroma and other organoleptic characteristics.

Concentration and/or Drying

The water or alcohol from the filtrate containing "non-steviol glycoside molecules" can be removed by any suitable means, including, but not limited to evaporation under reduced pressure or vacuum nano-filtration, freeze drying, flash drying, spray drying or a combination thereof to provide a concentrated or dried composition comprising "non-steviol glycoside molecules". The dried compositions may be optionally agglomerated, and/or granulated by compact or wet granulation techniques.

Chromatography

Non-steviol glycoside molecules and NSGCs of present invention may be further purified and separated using various chromatographic techniques including paper chromatography, thin layer chromatography, column chromatography, liquid chromatography (LC) medium pressure LC (MPLC), high performance LC (HPLC), ultra-high performance LC (UHPLC), flash column chromatography, displacement chromatography, affinity chromatography, supercritical fluid chromatography, ion-exchange chromatography, size-exclusion chromatography, adsorption chromatography, expanded bed adsorption chromatography, reversed-phase chromatography, normal-phase chromatography, hydrophilic interaction chromatography (HILIC), hydrophobic interaction chromatography, two-dimensional chromatography, simulated moving-bed chromatography (SMBC), countercurrent chromatography, and chiral chromatography—conducted at analytical, preparative, pilot or industrial scale.

In one embodiment, a chromatography system comprising a column packed with adsorption resin is used and the elution is achieved by applying alcoholic (e.g. Ethanol) solvent with gradient increase of concentration, to separate fractions enriched either with steviol glycosides or "non-steviol glycoside molecules".

In other embodiment, a chromatography system comprising a column packed with ion-exchange resin is used and the elution is achieved by applying acidic or alkaline solvent, to separate fractions enriched either with steviol glycosides or "non-steviol glycoside molecules".

In another embodiment, a chromatography system comprising plurality of consecutively connected columns packed with adsorption and/or ion-exchange resins is used, similar to one described in U.S. Pat. No. 8,981,081 which is incorporated herein in its entirety as reference.

In yet another embodiment, the separation is conducted by HPLC system with following configuration:
Agilent 1200 series HPLC—equipped with binary pump, auto sampler, column oven and DAD detector;
HPLC Column—Poroshell 120 SB-C18, 4.6×150 mm, 2.7 μm at 40° C.;
Injection volume—5 μL;
Detector—UV 210 nm;
Mobile phase A—25:75 (% v/v) Acetonitrile and buffer (10 mmol/L sodium phosphate buffer with pH 2.6);
Mobile phase B—32:68 (% v/v) Acetonitrile and buffer (10 mmol/L sodium phosphate buffer with pH 2.6);
Mobile phase gradient:
0 min—100% A, 0% B
12 min—100% A, 0% B
12.5 min—50% A, 50% B
13 min—0% A, 100% B
40 min—0% A, 100% B
Flow rate—0.5 mL/min;
Run time—45 minutes;
Post time—10 minutes.

Crystallization

Non-steviol glycoside molecules and NSGCs of present invention may be further purified and separated using various crystallization techniques including but not limited to cooling crystallization, evaporative crystallization, fractional crystallization, salting out etc.

In some embodiments, the crystallization may be conducted at concentrations ranging from 0.1% to 99% (w/w).

In some embodiments the crystallization is carried out from solvent comprising at least one solvent selected from the group including water, ethanol, methanol, n-propanol, isopropanol, n-butanol, chloroform, toluene, benzene, xylene, carbon tetrachloride, cyclohexane, 1,2-dichloroethane, dichloromethane, diethyl ether, dimethyl formamide, ethyl acetate, heptane, hexane, methyl-tert-butyl ether, pentane, 2,2,4-trimethylpentane, acetone, tetrahydrofuran, formic acid, acetic acid, and combinations thereof.

In yet another embodiment, the crystallization is achieved by adding a base, or alkali, or salt, or acid or any other agent capable of forming less soluble derivatives of non-steviol glycoside molecules, and wherein further process may include a step to convert the derivatised non-steviol glycoside molecule back into native state.

In other embodiments, the temperature of crystallization may vary from −20° C. to 80° C. In some embodiments, the temperature increase and/or decrease may be done by gradient method.

In other embodiments, the polarity of the solvent or solvent mixture used in crystallization varies from non-polar to polar. Including solvents which dielectric constant ranges from 1 to 88.

In some embodiment the ionic strength of the crystallization solution varies from 0 mol/L to 20 mol/L.

In other embodiment, the pH of the crystallization solution varies from 1 to 12.

Liquid-Liquid and Solid Liquid Extraction

NSGCs comprising non-steviol glycoside molecules of present invention, or derivatives thereof, may be further purified and separated using various solid-liquid and liquid-liquid extraction techniques including but not limited to dispersive liquid-liquid extraction, direct organic extraction, continuous countercurrent extraction, multistage continuous countercurrent extraction, centrifugal extraction, aqueous two-phase extraction, polymer-polymer extraction, polymer-salt extraction etc.

Suitable solvents include water and organic solvents selected from the group including ethanol, methanol, n-propanol, isopropanol, n-butanol, chloroform, toluene, benzene, xylene, carbon tetrachloride, cyclohexane, 1,2-dichloroethane, dichloromethane, diethyl ether, dimethyl formamide, ethyl acetate, heptane, hexane, methyl-tert-butyl ether, pentane, 2,2,4-trimethylpentane, acetone, tetrahydrofuran, formic acid, acetic acid, and combinations thereof.

Membrane Separation

NSGCs comprising non-steviol glycoside molecules of present invention, or derivatives thereof, may be further purified and separated using various membrane separation techniques including ultrafiltration, nanofiltration, reverse osmosis, dialysis, forward osmosis, electrodialysis, electrodeionization, electrofiltration, crossflow filtration, tangential flow filtration, dead-end filtration, spiral would membrane filtration, hollow fiber membrane filtration, cartridge filtration, cascade membrane filtration etc.

Consumables with NSGCs

One embodiment of present invention is a NSGC comprising at least one non-steviol glycoside molecule.

In some embodiments, the NSGC imparts sweet taste.

In one embodiment, the present invention is a sweetener composition comprising NSGC.

In another embodiment, the present invention is NSGC which is used in consumable as source of antioxidant, dietary fiber, fatty acids, vitamins, minerals, preservatives, hydration agents, probiotics, prebiotics, weight management agents, osteoporosis management agents, phytoestrogens, long chain primary aliphatic saturated alcohols, phytosterols and combinations thereof.

In another embodiment, the present invention is a flavor-enhancing composition comprising NSGC, wherein the NSGC is present in an amount effective to provide a concentration at or below the threshold flavor recognition level of the NSGC when the flavor-enhancing composition is added to a consumable. In a particular embodiment, the NSGC is present in an amount effective to provide a concentration below the threshold flavor recognition level of the NSGC when the flavor-enhancing composition is added to a consumable. In one embodiment, the NSGC is present in an amount effective to provide a concentration at least about 1%, at least about 5%, at least about 10%, at least about 15,% at least about 20% or at least about 25% or more below the threshold flavor recognition level of the NSGC when the flavor-enhancing composition is added to a consumable.

In yet another embodiment, the present invention is a sweetness-enhancing composition comprising NSGC, wherein the NSGC is present in an amount effective to provide a concentration at or below the threshold sweetness recognition level of the NSGC when the sweetness-enhancing composition is added to a consumable. In a particular embodiment, the NSGC is present in an amount effective to provide a concentration below the threshold sweetness recognition level of the NSGC when the sweetness-enhancing composition is added to a consumable. In one embodiment, the NSGC is present in an amount effective to provide a concentration at least about 1%, at least about 5%, at least about 10%, at least about 15,% at least about 20% or at least about 25% or more below the threshold sweetness recognition level of the NSGC when the sweetness-enhancing composition is added to a consumable.

In yet another embodiment, the present invention is a consumable comprising NSGC. Suitable consumables include, but are not limited to, liquid-based or dry consumables, such as, for example, pharmaceutical compositions, edible gel mixes and compositions, dental compositions, foodstuffs, beverages and beverage products.

In a particular embodiment, the present invention is a beverage comprising NSGC. In a particular embodiment, the NSGC is present in the beverage at a concentration that is above, at or below the threshold sweetness recognition concentration of the NSGC.

In another particular embodiment, the present invention is a beverage product comprising NSGC. In a particular embodiment, the NSGC is present in the beverage product at a concentration that is above, at or below the threshold flavor recognition concentration of the NSGC.

In another aspect, the present invention is a method of preparing a consumable comprising (i) providing a consumable matrix and (ii) adding NSGC to the consumable matrix to provide a consumable. In a particular embodiment, the NSGC is present in the consumable in a concentration above, at or below the threshold sweetness recognition of the NSGC. In another particular embodiment, the NSGC is present in the consumable in a concentration above, at or below the threshold flavor recognition of the NSGC.

In a particular embodiment, the present invention is a method of preparing a beverage comprising (i) providing a beverage matrix and (ii) adding NSGC to the consumable matrix to provide a beverage. In a particular embodiment, the NSGC is present in the consumable in a concentration above, at or below the threshold sweetness recognition of the NSGC. In another particular embodiment, the NSGC is present in the consumable in a concentration above, at or below the threshold flavor recognition concentration of the NSGC.

In another aspect, the present invention is a method of enhancing the sweetness of a consumable comprising (i) providing a consumable comprising at least one sweet ingredient and (ii) adding NSGC to the consumable to provide a consumable with enhanced sweetness, wherein the NSGC is present in the beverage with enhanced sweetness at a concentration at or below the threshold sweetness recognition concentration of the NSGC.

In a particular embodiment, the present invention is a method of enhancing the sweetness of a beverage comprising (i) providing a beverage comprising at least one sweet ingredient and (ii) adding NSGC to the beverage to provide a beverage with enhanced sweetness, wherein the NSGC is present in the beverage with enhanced sweetness at a concentration below the threshold sweetness recognition concentration of the NSGC. In one embodiment, the concentration of the NSGC is present in the beverage with enhanced sweetness at a concentration that is at least about 1%, at least about 5%, at least about 10%, at least about 15%, at least about 20%, or at least about 25% or more below the threshold sweetness recognition concentration of the NSGC.

In a further aspect, the present invention is a method of enhancing the flavor of a consumable comprising (i) providing a consumable comprising at least one flavor ingredient and (ii) adding NSGC to the consumable to provide a consumable with enhanced flavor, wherein the NSGC in present in the consumable with enhanced flavor at a concentration at or below the threshold flavor recognition concentration of the NSGC.

In a particular embodiment, the present invention is a method of enhancing the flavor of a beverage comprising (i) providing a beverage comprising at least one flavor ingredient and (ii) adding NSGC to the beverage to provide a beverage with enhanced flavor, wherein the NSGC is present in the beverage with enhanced flavor in a concentration at or below the threshold flavor recognition concentration of the NSGC. In one embodiment, the concentration of the NSGC is present in the beverage with enhanced sweetness at a concentration that is at least about 1%, at least about 5%, at least about 10%, at least about 15%, at least about 20%, or at least about 25% or more below the threshold flavor recognition concentration of the NSGC.

In the above methods, the NSGC may be added as such, or in the form of a composition comprising the NSGC. When the NSGC is provided as a composition, the concentration of the NSGC in the composition is effective to provide a concentration above, at or below the threshold flavor or sweetener composition of the NSGC, when the composition is added to the consumable, e.g., the food or beverage.

In some embodiments, the compositions of the present invention further comprise one or more mogrosides, where the mogrosides are selected from, but not limited to, the group consisting of Luo han guo extract, by-products of other mogrosides' isolation and purification processes, a commercially available Luo han guo extract, mogroside IIE, mogroside IIB, mogroside III, mogroside IV, mogroside V, 11-oxo-mogroside V, mogroside VI, siamenoside I, grosmomoside I, neomogroside, and other mogrol and oxo-mogrol glycosides occurring in Sirailia grosvenorii fruit and combinations thereof.

In other embodiments, the compositions of the present invention further comprise one or more sweeteners or additional sweeteners. In one embodiment, the additional sweetener is a natural sweetener or a synthetic sweetener. In a particular embodiment, the additional sweetener is a high intensity sweetener. In a particular embodiment, the additional sweetener is a mogroside.

In some embodiments, the compositions of the present invention further comprise one or more additives. In a particular embodiment, the additive is selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

In some embodiments, the compositions of the present invention further comprise one or more functional ingredients. In a particular embodiment, the functional ingredient is selected from the group consisting of caffeine, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In a particular embodiment, the present invention is a consumable comprising a NSGC and one or more sweeteners, additional sweeteners, additives or functional ingredients.

In another particular embodiment, the present invention is a beverage comprising NSGC and one or more sweeteners, additional sweeteners, additives or functional ingredients.

The NSGCs can be used either alone or in combination with at least one other sweetener in consumables including food, beverage, pharmaceutical composition, tobacco, nutraceutical, oral hygienic composition, or cosmetic. The other sweeteners are selected from the group including sucrose, glyceraldehyde, dihydroxyacetone, erythrose, threose, erythrulose, arabinose, lyxose, ribose, xylose, ribulose, xylulose, allose, altrose, allulose, galactose, glucose, gulose, idose, mannose, talose, fructose, psicose, sorbose, tagatose, mannoheptulose, sedoheltulose, octolose, fucose, rhamnose, arabinose, turanose, sialose, inulin, inulooligosaccharides, fructooligosaccharides, high fructose corn syrup (HFCS), maltodextrin, coupling sugar, honey, stevia, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, dulcoside A, dulcoside B, rubusoside, steviolbioside, stevioside, other steviol glycosides occurring in Stevia rebaudiana plant, biosynthetic steviol glycosides, glycosylated steviol glycosides, glucosylated steviol glycosides (GSGs), mogroside IV, mogroside V, mogroside VI, Luo han guo, siamenoside, other mogrosides occurring in Siraitia grosvenorii fruits, monatin and its salts, curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, and cyclocarioside I, sugar alcohols, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, and combinations thereof.

The following examples illustrate preferred embodiments of the invention. It will be understood that the invention is not limited to the materials, proportions, conditions and procedures set forth in the examples, which are only illustrative.

Example 1

Preparation of NSGC

Five kilograms of dried Stevia rebaudiana leaves (having about 8% (w/w) moisture content and about 10% (w/w, dried basis) total steviol glycosides) were ground to 10-20 mm particles. The dried leaf material was loaded into an extraction tank and the extraction was carried out with 100 L of RO water at 65° C. for 10 min. The insoluble matter was removed by filtration. The yellowish filtrate was collected and fed a column packed with 8.5 L of polymeric macroporous adsorbent resin (YWD-03, Cangzhou Yuanwei, China), with about 50 L/hour flow rate. After completion of filtrate, the column was additionally washed with 45 L of water and both effluents were combined. The combined solution was evaporated under vacuum, at the temperature between 30° C.-35° C., to a final volume of 10 L.

The majority of steviol glycosides were absorbed on macroporous adsorbent resin and were eluted with about 45 L of 70% aqueous Ethanol. Aqueous Ethanol eluate was further processed to yield about 400 g stevia extract with about 96% w/w total steviol glycosides content.

The above-mentioned 10 L combined and evaporated solution was mixed with 90 L of pure Ethanol and the mixture was maintained for 10 min with slow agitation. The resulting precipitate was removed by vacuum filtration. The filtrate was collected and then subjected to vacuum evaporation (at 30° C.-35° C.) to remove ethanol and to further concentrate to about 4 L of NSGC in syrup form containing 22% w/w solids. The HPLC assay of this solution shows about 1.3% residual steviol glycosides wherein the % ratio of individual steviol glycosides was: Rebaudioside E 0.41%, Rebaudioside O 10.52%, Rebaudioside D 5.95%, Rebaudioside N 1.49%, Rebaudioside M 3.07%, Rebaudioside A 56.98%, Stevioside 11.66%, Rebaudioside F 0.89%, Rebaudioside C 4.37%, Dulcoside A 0.11%, and Rebaudioside B 0.35%. The concentrate was dried using vacuum evaporation followed by drying in vacuum oven at 30° C.-35° C.

Example 2

Extraction of NSGC by Aqueous Ethanol

A 50 kg of dried Stevia rebaudiana leaves (having about 8% (w/w) moisture content and about 8.5% (w/w) total steviol glycosides) were ground to 10-20 mm particles. The HPLC assay of this leaf also shows about 3.2% w/w total CGA content comprising of 1.34% CGAs (neo-CGA, n-CGA & crypto-CGA), and 1.86% iso-CGAs (iso-CGA-B, iso-CGA-A & iso-CGA-C). The dried leaf material was loaded into an extraction tank and the extraction was carried out with 800 L of 30% (v/v) Ethanol at 65° C. for 30 min. The mixture was filtered through 800 g of diatomaceous earth. The yellowish filtrate was collected and cooled down to 30° C. The EtOH was removed from the filtrate by nanofiltration membrane (NF90-400, Dow Chemical Company, USA) at 45° C. under pressure of 0.5-0.8 MPa.

320 L of the retentate obtained from nanofiltration estimated to contain about 1.57 kg of total CGAs and 4.1 kg of total steviol glycosides was fed to column packed with 125 L of polymeric macroporous adsorbent resin (YWD-03, Cangzhou Yuanwei, China), at about 125 L/hour flow rate. After feeding the retentate, the column was additionally washed with 62.5 L of water and both effluents were combined to make flow-through product, which was further concentrated using nanofiltration membrane (NF90-400, Dow Chemical Company, USA) to 20% total solids content. Flocculation of the concentrated flow-through product was carried out by using 9 volumes of Ethanol. The flocculated precipitate was separated by filtration and the Ethanol was removed by nanofiltration membrane (NF90-400, Dow Chemical Company, USA) as mentioned above. The concentrate was dried using freeze-dryer. The purified flow-through product contained 12.24% w/w (dry basis) of total CGA, which comprised of neo-CGA 2.65%, n-CGA 7.46%, crypto-CGA 1.84%, iso-CGA-B 0.07%, iso-CGA-A 0.16% and iso-CGA-C 0.06% and 0.70% w/w of total steviol glycosides.

The adsorbed CGAs were eluted from the macroporous adsorbent resin using 690 L of 25% (v/v) Ethanol. The solution was passed through nanofiltration membrane (NF90-400, Dow Chemical Company, USA) to remove Ethanol and then dried by freeze-dryer as mentioned above to make 25%-Ethanol product. The 25%-Ethanol product contained 19.52% w/w of total CGA, which comprised of neo-CGA 0.78%, n-CGA 3.59%, crypto-CGA 1.04%, iso-CGA B 2.64%, iso-CGA-A 4.14% and iso-CGA-C 7.33%, and 12.28% w/w of total steviol glycosides including Rebaudioside E 1.43%, Rebaudioside D 1.54%, Rebaudioside A 5.31%, Stevioside 2.49% and others.

The remaining steviol glycosides were eluted from macroporous adsorbent resin with about 380 L of 70% aqueous Ethanol and further processed to yield *stevia* extract with TSG content of 71%.

Example 3

Extraction of NSGC by water 50 kg of *Stevia rebaudiana* dried leaf material, similar to one used in Example 2, was loaded into an extraction tank and the extraction was carried out with 800 L of water at 90° C. for 30 min. The mixture was filtered through 800 g of diatomaceous earth. The yellowish filtrate was collected and cooled down to 30° C., and was fed into a column packed with 125 L of polymeric macroporous adsorbent resin (YWD-03, Cangzhou Yuanwei, China). The subsequent steps were similar to ones described in Example 2.

The flow-through product contained 14.47% w/w of total CGA, which comprised of neo-CGA 4.67%, n-CGA 5.67%, crypto-CGA 3.44%, iso-CGA-B 0.24%, iso-CGA-A 0.21% and iso-CGA-C 0.24% and 0.59% w/w of total steviol glycosides. The 25%-Ethanol product contained 17.97% w/w of total CGA, comprised of neo-CGA 0.78%, n-CGA 1.56%, crypto-CGA 0.91%, iso-CGA-B 5.36%, iso-CGA-A 3.21% and iso-CGA-C 6.15% and 13.83% w/w of total steviol glycosides, including Rebaudioside E 2.89%, Rebaudioside D 1.52%, Rebaudioside A 5.31%, Stevioside 2.49% and others.

Example 4

Purification of Non-Steviol Glycoside Composition (NSGC) Using Liquid-Liquid Extraction One gram of 25%-Ethanol product of obtained in Example 3 was mixed well with 20 mL of RO water. The pH of the mixture was adjusted to pH 4 using 4% (v/v) phosphoric acid. After pH adjustment, ethyl acetate was added into the mixture at ratio of 1:1 (v/v, water:ethyl acetate). The extraction of aqueous solution was carried out with ethyl acetate for 5 min at room temperature and ethyl acetate fraction was separated from aqueous fraction by means of separation funnel. This step was repeated another 2 times to obtain three ethyl acetate fractions. 10 mL of water was added into each ethyl acetate fraction. The ethyl acetate was removed by vacuum evaporation. The aqueous residue after removal of ethyl acetate was freeze-dried.

The combined weight of three freeze-dried samples was 0.2 g. The combined ethyl acetate fractions contained 68.53% w/w (dried basis) of total CGAs, comprising of neo-CGA 0.10%, n-CGA 1.24%, crypto-CGA 0.52%, iso-CGA-B 20.33%, iso-CGA-A 15.99% and iso-CGA-C 30.36%.

Example 5

Extraction of NSGC by Water 50 kg of *Stevia rebaudiana* dried leaf material, similar to one used in Example 2, was loaded into an extraction tank and the extraction was carried out with 800 L of water at 65° C. for 30 min. The mixture was filtered through 800 g of diatomaceous earth. The yellowish filtrate was collected and cooled down to 30° C., and was fed into a column packed with 125 L of polymeric macroporous adsorbent resin (W/D-03, Cangzhou Yuanwei, China). The subsequent process was similar to one described in Example 2. The 25%-Ethanol product contained 19.90% w/w of total CGA, which comprised of neo-CGA 0.35%, n-CGA 4.30%, crypto-CGA 1.23%, iso-CGA-B 0.81%, iso-CGA-A 8.19% and iso-CGA-C 5.02% and 13.47% w/w of total steviol glycosides, including Rebaudioside D 1.86%, Rebaudioside A 7.45%, Stevioside 2.13% and others.

Example 6

Purification of NSGC

6 Grams of the dried 25%-Ethanol product of Example 3 was dissolved in 20 mL of water. 180 mL of pure Ethanol was added to the mixture and stirred at room temperature for 1 hour. The obtained suspension was filtered, and 0.72 g of activated carbon was added to the filtrate and allowed to stir at room temperature for another 1 hour. The mixture was filtered again to remove the activated carbon. The obtained filtrate was concentrated using rotary evaporator at 40° C. and dried in vacuum oven at 40° C. to give 3.6 g of processed 25%-Ethanol product. The processed 25%-Ethanol product contained 22.32% w/w of total CGA, including neo-CGA 0.84%, n-CGA 1.26%, crypto-CGA 0.91%, iso-CGA B 6.85%, iso-CGA-A 4.99% and iso-CGA-C 7.48%, and 23.26% w/w of total steviol glycosides including Rebaudioside D 2.03%, Rebaudioside A 12.18%, Stevioside 6.70% and others.

Example 7

Membrane Purification of NSGC

One gram of the processed 25%-Ethanol product of Example 6 was dissolved in 100 mL of RO water and the solution was fed into the Sterlitech HP4750 high-pressure stirred cell filtration system (Sterlitech Corporation, USA) at 20° C., until 50 mL of permeate was collected. Both retentate and permeate were freeze-dried and tested by HPLC.

The experiment was repeated using different 47 mm membrane discs obtained from Sterlitech Corporation (USA). Particularly GE 2000 UFGH (Sterlitech Cat. No. YMGHSP475), GE 1000 (Sterlitech Cat. No. YMGESP475), Synder NFG (Sterlitech Cat. No. YMNFG475), Microdyn Nadir NP010 (Sterlitech Cat. No. YMNP010475), Evonik Duramem 900 (Sterlitech Cat. No. 1120773) and Synder XT, PES, UF (Sterlitech Cat. No. YMXT475).

The permeate and retentate analysis results are summarized in Table 1.

repeated to collect another 50 mL of the permeate. This process was repeated to obtain ten permeate fraction. The retentate and the permeates were freeze dried and tested by HPLC.

For retentate, the total CGA was 16.51% (w/w, dry basis), comprised of neo-CGA 0.35%, n-CGA 0.65%, crypto-CGA 1.11%, iso-CGA-B 5.52%, iso-CGA-A 2.75% and iso-CGA-C 6.13% and the total steviol glycoside content was 37.69% w/w, including Rebaudioside D 2.75%, Rebaudioside A 20.48%, Stevioside 10.39%, Rebaudioside C 1.35% and others. For combined sample of 10 permeate samples, the total CGA was 30.33% (w/w, dry basis), comprised of neo-CGA 0.97%, n-CGA 2.52%, crypto-CGA 2.28%, iso-CGA-B 8.23%, iso-CGA-A 8.24% and iso-CGA-C 8.08%, and the total steviol glycoside content was 5.99% w/w, including Rebaudioside A 2.66%, Stevioside 2.89% and others.

TABLE 1

Permeate and Retentate HPLC assay

| | Sample ID | Initial | GE 2000 UFGH Ret* | GE 2000 UFGH Per* | GE 1000 Ret | GE 1000 Per | Synder NFG Ret | Synder NFG Per | Microdyn Nadir NP010 Ret | Microdyn Nadir NP010 Per | Evonik Duramem 900 Ret | Evonik Duramem 900 Per | Synder XT, PES, UF Ret | Synder XT, PES, UF Per |
|---|---|---|---|---|---|---|---|---|---|---|---|---|---|---|
| CGA's | neo-CGA | 0.84 | 0.87 | 1.23 | 0.88 | 1.15 | 0.88 | 0.07 | 1.09 | 0.62 | 1.08 | 0.14 | 0.88 | 0.62 |
| HPLC | n-CGA | 1.26 | 1.26 | 2.22 | 1.28 | 2.15 | 1.33 | 0.11 | 1.41 | 1.07 | 1.41 | 0.15 | 1.33 | 0.96 |
| assay | crypto-CGA | 0.91 | 0.91 | 1.55 | 0.93 | 1.52 | 0.96 | 0.08 | 1.02 | 0.81 | 1.02 | 0.13 | 0.93 | 0.72 |
| % (as | iso-CGA-B | 6.85 | 7.14 | 6.88 | 6.96 | 5.96 | 7.09 | 0.03 | 7.47 | 2.89 | 6.99 | 0.44 | 7.54 | 2.13 |
| dried) | iso-CGA-A | 4.99 | 4.99 | 7.95 | 5.03 | 7.17 | 5.21 | 0.02 | 5.27 | 3.04 | 5.11 | 0.38 | 5.32 | 2.17 |
| | iso-CGA-C | 7.48 | 7.77 | 7.11 | 7.63 | 5.94 | 7.76 | 0.03 | 7.92 | 2.65 | 7.60 | 0.38 | 7.93 | 1.83 |
| | Total CGA | 22.32 | 22.94 | 26.93 | 22.71 | 23.90 | 23.23 | 0.34 | 24.18 | 11.08 | 23.22 | 1.62 | 23.93 | 8.44 |
| SG's | Reb E | 0.32 | 0.35 | 0.00 | 0.96 | 0.00 | 1.15 | 0.00 | 0.51 | 0.00 | 0.80 | 0.31 | 0.89 | 0.47 |
| HPLC | Reb O | 0.20 | 0.21 | 0.05 | 0.15 | 0.00 | 0.18 | 0.00 | 0.10 | 0.00 | 0.12 | 0.22 | 0.14 | 0.00 |
| Assay | Reb D | 2.03 | 2.02 | 0.12 | 1.80 | 0.10 | 1.73 | 0.15 | 2.01 | 0.00 | 1.70 | 0.22 | 1.81 | 0.23 |
| % (as | Reb N | 0.34 | 0.38 | 0.00 | 0.43 | 0.00 | 0.43 | 0.06 | 0.27 | 0.00 | 0.35 | 0.04 | 0.39 | 0.03 |
| dried) | Reb M | 0.36 | 0.39 | 0.00 | 0.38 | 0.00 | 0.34 | 0.00 | 0.26 | 0.00 | 0.36 | 0.00 | 0.39 | 0.04 |
| | Reb A | 12.18 | 13.31 | 1.79 | 12.65 | 1.10 | 12.71 | 1.00 | 12.93 | 1.23 | 12.62 | 1.51 | 12.87 | 1.71 |
| | Stev | 6.70 | 7.29 | 1.91 | 6.92 | 1.30 | 6.97 | 0.59 | 6.98 | 1.57 | 6.80 | 0.97 | 6.91 | 1.17 |
| | Reb F | 0.16 | 0.20 | 0.07 | 0.18 | 0.04 | 0.18 | 0.11 | 0.18 | 0.05 | 0.16 | 0.21 | 0.18 | 0.03 |
| | Reb C | 0.81 | 0.87 | 0.11 | 0.83 | 0.08 | 0.83 | 0.08 | 0.83 | 0.12 | 0.81 | 0.09 | 0.78 | 0.12 |
| | Dul A | 0.04 | 0.05 | 0.05 | 0.05 | 0.09 | 0.04 | 0.12 | 0.05 | 0.02 | 0.04 | 0.15 | 0.05 | 0.02 |
| | Rub | 0.03 | 0.03 | 0.19 | 0.02 | 0.17 | 0.03 | 0.02 | 0.03 | 0.04 | 0.02 | 0.04 | 0.03 | 0.01 |
| | Reb B | 0.06 | 0.08 | 0.02 | 0.09 | 0.00 | 0.07 | 0.02 | 0.14 | 0.19 | 0.05 | 0.02 | 0.09 | 0.01 |
| | Sbio | 0.04 | 0.04 | 0.03 | 0.03 | 0.00 | 0.03 | 0.02 | 0.06 | 0.07 | 0.03 | 0.01 | 0.06 | 0.00 |
| | Total SG | 23.26 | 25.22 | 4.34 | 24.49 | 2.89 | 24.69 | 2.17 | 24.34 | 3.30 | 23.86 | 3.79 | 24.58 | 3.86 |

*Note:
Ret: Retentate;
Per: Permeate

The membrane GE 1000 was selected for further experiments.

Example 8

Purification of NSGC Using Membrane with Diafiltration Step

One gram of processed 25%-Ethanol product of Example 6 was mixed with 100 mL of RO water and was fed into the Sterlitech HP4750 high-pressure stirred cell filtration system (Sterlitech Corporation, USA) fitted with GE 1000 (Sterlitech Cat No YMGESP475) at 20° C., until 50 mL of permeate was collected. After collecting 50 mL of permeate, 50 mL of RO water was added into the cell and filtration was

Example 9

Purification of NSGC Using Adsorption Chromatography System 100 mL water solution containing 10.07 g 25%-Ethanol product from Example 5 was fed to a column packed with 300 mL of polymeric macroporous adsorbent resin (TF3, Cangzhou Yuanwei, China), at about 300 mL/hour flow rate at room temperature. After completion of loading, the column was additionally washed with 600 mL of water and both effluents were combined and collected as flow-through product. The flow-through product was concentrated by nanofiltration membrane (NF90-400, Dow Chemical Company, USA) and then dried using spray dryer to obtain 1.9 g dried flow through product containing 27.82% w/w (dry basis) of total CGAs, comprised of neo-CGA 4.11%, n-CGA 17.21%, crypto-CGA 6.25%, iso-CGA-B 0.04%, iso-CGA-A 0.17% and iso-CGA-C 0.04% and 0.12% w/w of total steviol glycosides.

The adsorbed CGAs were eluted from the macroporous adsorbent resin using 1,500 mL of 20% (v/v) Ethanol. The solution was passed through nanofiltration membrane (NF90-400, Dow Chemical Company, USA) to remove Ethanol and to concentrate. The concentrate was dried by using spray dryer and 4.3 g dried sample was collected as 20%-Ethanol product. This product contained 21.99% w/w of total CGA, comprised of neo-CGA 0.03%, n-CGA 0.23%, crypto-CGA 0.16%, iso-CGA-B 2.39%, iso-CGA-A 11.93% and iso-CGA-C 7.25% and 2.18% w/w of total steviol glycosides.

The remaining steviol glycosides absorbed on macroporous resin were eluted with about 900 mL of 60% aqueous Ethanol and processed further to yield 3.6 g of *stevia* extract containing 60.50% w/w total steviol glycosides.

Example 10

Purification of NSGC Using Adsorption Chromatography System 100 mL water solution containing 9.0 g 25%-Etahnol product from Example 5 was fed to a column packed with 300 mL of polymeric macroporous adsorbent resin (TF3, Cangzhou Yuanwei, China), with about 300 ml/hour flow rate at room temperature. After completion of loading, the column was additionally washed with 900 mL of water and both effluents were combined and collected as flow-through product. The product was concentrated by using nanofiltration membrane (NF90-400, Dow Chemical Company, USA) and then spray dried to yield 1.51 g of dried flow-through product containing 31.27% w/w (dry basis) of total CGA, comprised of neo-CGA 4.19%, n-CGA 19.35%, crypto-CGA 7.10%, iso-CGA-B 0.11%, iso-CGA-A 0.43% and iso-CGA-C 0.10% and 0.01% w/w of total steviol glycosides.

The macroporous adsorbent resin then sequentially washed with 900 mL of 15% (v/v) Ethanol, 900 mL of 20% (v/v) Ethanol, 900 mL of 25% (v/v) Ethanol and 900 mL of 60% (v/v) Ethanol. All the collected solutions were concentrated by using nanofiltration membrane (NF90-400, Dow Chemical Company, USA) and then dried using spray dryer to obtain 15%-Ethanol product, 20%-Ethanol product, 25%-Ethanol product and 60%-Ethanol product, respectively. The HPLC assay of these fractions is summarized in Table 2.

TABLE 2

HPLC assay of eluate fractions

| | HPLC assay % (as dried) | | | | | | | |
| --- | --- | --- | --- | --- | --- | --- | --- | --- |
| Fraction | neo-CGA | n-CGA | crypto-CGA | iso-CGA-B | iso-CGA-A | iso-CGA-C | Total CGA | Total SG |
| Flow-through | 4.19 | 19.35 | 7.10 | 0.11 | 0.43 | 0.10 | 31.27 | 0.01 |
| 15%-Ethanol | 0.04 | 0.11 | 0.06 | 4.04 | 14.43 | 3.97 | 22.65 | 0.11 |
| 20%-Ethanol | 0.01 | 0.02 | 0.01 | 0.77 | 9.84 | 17.24 | 27.89 | 0.93 |
| 25%-Ethanol | 0.01 | 0.03 | 0.01 | 0.13 | 1.66 | 16.62 | 18.46 | 9.30 |
| 60%-Ethanol | 0.00 | 0.00 | 0.00 | 0.02 | 0.10 | 0.18 | 0.30 | 48.81 |

Example 11

Purification of NSGC Using Adsorption Chromatography System 100 mL water solution containing 9.0 g 25%-Ethanol product from Example 5 was fed to a column packed with 300 mL of polymeric macroporous adsorbent resin (TF3, Cangzhou Yuanwei, China), with about 300 ml/hour flow rate at room temperature. After completion of loading, the column was additionally washed with 600 mL of water and both effluents are combined and collected as flow-through product. The flow-through product was concentrated by using nanofiltration membrane (NF90-400, Dow Chemical Company, USA) and then dried to yield 1.45 g dried flow-through product containing 18.04% w/w (dry basis) of total CGA, comprised of neo-CGA 2.12%, n-CGA 13.40%, crypto-CGA 2.47%, iso-CGA-A 0.04% and iso-CGA-C 0.01% and 0.74% w/w of total steviol glycosides.

The macroporous adsorbent resin was then sequentially washed with 1500 mL of 20% (v/v) Ethanol and 900 mL of 60% (v/v) Ethanol. All the collected solutions were concentrated by using nanofiltration membrane (NF90-400, Dow Chemical Company, USA) and then dried to obtain 20%-Ethanol product and 60%-Ethanol product, respectively.

The HPLC assay of these fractions is summarized in Table 3.

TABLE 3

HPLC assay of eluate fractions

| Fraction | HPLC assay % (as dried) | | | | | | | |
|---|---|---|---|---|---|---|---|---|
| | neo-CGA | n-CGA | crypto-CGA | iso-CGA-B | iso-CGA-A | iso-CGA-C | Total CGA | Total SG |
| Flow-through | 2.12 | 13.40 | 2.47 | 0.00 | 0.04 | 0.01 | 18.04 | 0.74 |
| 20%-Ethanol | 0.07 | 0.87 | 0.27 | 1.97 | 15.85 | 5.31 | 24.34 | 0.21 |
| 60%-Ethanol | 0.00 | 0.01 | 0.00 | 0.06 | 0.42 | 0.70 | 1.20 | 48.51 |

Example 12

Purification of NSGC Using Adsorption Chromatography System 500 mg/L water solution of 25%-Etahnol product from Example 5 was fed to a column packed with 150 mL of polymeric macroporous adsorbent resin (TF3, Cangzhou Yuanwei, China), with about 150 mL/hour flow rate at room temperature. The effluent was collected and its sweetness was periodically analyzed by sensory method. The feeding was stopped when the sweetness was detected in effluent. The effluents were combined, concentrated and then dried using spray dryer to obtain effluent product containing 21.65% w/w (dry basis) of total CGAs, comprised of neo-CGA 1.37%, n-CGA 5.42%, crypto-CGA 1.97%, iso-CGA-B 1.90%, iso-CGA-A 6.12% and iso-CGA-C 4.87% and 0.42% w/w of total steviol glycosides.

The macroporous adsorbent resin was then sequentially washed with 300 mL of 20% (v/v) Ethanol and 450 mL of 60% (v/v) Ethanol. All the collected solutions were concentrated by using nanofiltration membrane (NF90-400, Dow Chemical Company, USA) and then dried using spray dryer to obtain 20%-Ethanol product and 60%-Ethanol product, respectively.

The HPLC assay of these fractions is summarized in Table 4.

TABLE 4

HPLC assay of eluate fractions

| Fraction | HPLC assay % (as dried) | | | | | | | |
|---|---|---|---|---|---|---|---|---|
| | neo-CGA | n-CGA | crypto-CGA | iso-CGA-B | iso-CGA-A | iso-CGA-C | Total CGA | Total SG |
| Flow-through | 1.37 | 5.42 | 1.97 | 1.9 | 6.12 | 4.87 | 21.65 | 0.42 |
| 20%-Ethanol | 0.43 | 2.39 | 0.81 | 1.23 | 5.08 | 5.37 | 15.31 | 3.37 |
| 60%-Ethanol | 0 | 0.01 | 0 | 0.03 | 0.04 | 0.08 | 0.16 | 67.79 |

Example 13

Purification of NSGC Using Crystallization

1 Gram of the dried 25%-Ethanol product of Example 4 was dissolved in 20 mL of water. 100 mg of $Ca(OH)_2$ was added and the mixture was kept for 1 hour until a precipitate is formed. The obtained suspension was filtered and the precipitate was re-suspended in water and titrated with acetic acid until dissolution and was fed into a column packed with 100 mL of polymeric macroporous adsorbent resin (YWD-03, Cangzhou Yuanwei, China). The subsequent process was similar to one described in Example 2.

The 25%-Ethanol product contained 42.90% w/w of total CGA, which comprised of neo-CGA 0.51%, n-CGA 1.30%, crypto-CGA 0.34%, iso-CGA-B 5.78%, iso-CGA-A 6.89% and iso-CGA-C 28.08% and 0.3% w/w of total steviol glycosides, including, Rebaudioside A 0.2%, Stevioside 0.1% and others.

Example 14

Consumable comprising NSGC

Carbonated beverage samples were prepared according to formula presented in Table 5.

TABLE 5

Formula for carbonated beverages

| Ingredients | Quantity, % |
|---|---|
| Cola flavor | 0.340 |
| ortho-Phosphoric acid | 0.100 |
| Sodium citrate | 0.310 |
| Sodium benzoate | 0.018 |
| Citric acid | 0.018 |
| Sweetener composition | 0.050 |
| Carbonated water | to 100 |

The following samples were used as "sweetener composition" in the formula. (i) commercial sample of Rebaudioside A (97% pure), and (ii) mixture (with 95:5 w/v ratio) of commercial Rebaudioside A (97% pure) and NSGC prepared according to Example 4. The sensory assessment of beverage samples was conducted by 20 panelists. The results are summarized in Table 6.

TABLE 6

Sensory evaluation of carbonated beverage samples

| | "Sweetener composition" used in formula | | | | |
|---|---|---|---|---|---|
| | Sweetness Lingering* | Bitterness* | Delayed sweetness onset* | Licorice taste* | Overall taste |
| RebA 97 + NSGC (95:5) | 2 | 1 | 1 | 2 | pleasant |
| Pure RebA 97 | 5 | 5 | 5 | 5 | unpleasant |

*For "Sweetness Lingering", "Bitterness", "Delayed sweetness onset", and "Licorice taste" characteristics the panelists score between 1 to 5, where the lower score represents more pleasant taste sensation by panelist The results showed the beverages prepared using the sweetener composition comprising NSGC possessed the best organoleptic characteristics.

Example 15

Consumable Comprising Novel NSGC

Chocolate samples were prepared according to formula in Table 7.

TABLE 7

Formula for chocolate samples

| Ingredients | Quantity, % |
|---|---|
| Chocolate liquor | 30.0 |
| Cocoa butter | 11.5 |
| Milk powder | 14.0 |
| Sorbitol | 44.0 |
| Salt | 0.1 |
| Sweetener composition | 0.1 |
| Lecithin | 0.3 |

Chocolate liquor, cocoa butter, milk powder, sorbitol, salt, and the "sweetener composition" were kneaded sufficiently, and the mixture was then placed in a refiner to reduce its particle size for 24 hours. Thereafter, the content was transferred into a conche, the lecithin was added, and the composition was kneaded at 50° C. for 48 hours. Then, the content was placed in a shaping apparatus, and solidified.

The following samples were used as "sweetener composition" in the formula of Table 3. (i) Commercial sample of Rebaudioside A (97% pure), and (ii) mixture (with 95:5 w/v ratio) of commercial Rebaudioside A (97% pure) and NSGC prepared according to Example 4. The sensory assessment of chocolate samples was conducted by 20 panelists. The results are summarized in Table 8.

TABLE 8

Sensory evaluation of chocolate samples

| | "Sweetener composition" used in formula | | | |
|---|---|---|---|---|
| | Sweetness Lingering* | Bitterness* | Licorice taste* | Overall taste |
| RebA 97 + NSGC (95:5) | 1 | 2 | 2 | pleasant |
| Pure RebA 97 | 5 | 5 | 5 | unpleasant |

*For "Sweetness Lingering", "Bitterness", and "Licorice taste" characteristics the panelists score between 1 to 5, where the lower score represents more pleasant taste sensation by panelist The results showed the chocolate samples prepared using the sweetener composition comprising NSGC possessed the best organoleptic characteristics.

Example 16

Purification of Non-Steviol Glycoside Composition (NSGC) Using Liquid-Liquid Extraction One hundred grams of processed 25%-Ethanol Product, prepared according to Example 6, was mixed with 2,000 mL of RO water. Then 2,000 mL ethyl acetate was added and the mixture was stirred for 2 hrs. The ethyl acetate fraction was separated, evaporated by rotary vacuum evaporator and dried at 40° C. for 12 hrs to yield 20.60 g NSCG extract containing 65.01% w/w (dried basis) of Total CGA, comprising: neo-CGA 0.05%, n-CGA 1.24%, crypto-CGA 0.49%, iso-CGA-B 8.98%, iso-CGA-A 22.78% and iso-CGA-C 31.46%.

Example 17

Purification of Non-Steviol Glycoside Composition (NSGC) Using Crystallization

Twenty grams of NSGC extract obtained in Example 16 was dissolved in 400 mL 0.1% (w/v) sodium hydroxide. The pH was adjusted to neutral by phosphoric acid and the solution was agitated at 25° C. for 3 days. After 3 days, the NSGC crystals were separated by filtration and dried at 40° C. The yield of the crystalline NSGC was 34.59%, containing 83.37% w/w (dried basis) of total CGA comprising: neo-CGA 0.01%, n-CGA 0.23%, crypto-CGA 0.06%, iso-CGA-B 2.73%, iso-CGA-A 12.20% and iso-CGA-C 68.14%.

Example 18

Purification of Non-Steviol Glycoside Composition (NSGC) Using Crystallization

Seven grams of crystalline NSGC of Example 17 was dissolved in 70 mL of water by heating the mixture. The solution was agitated at 25° C. for 2 days. After 2 days, the purified NSGC crystals were separated by filtration and dried at 40° C. The yield of the purified crystalline NSGC was 41.28%, containing 95.83% w/w (dried basis) of total CGA, comprising: iso-CGA-A 0.10% and iso-CGA-C 95.73%.

While the foregoing has described one or more embodiments of the present invention, it will be understood by those skilled in the art that various changes and modifications may be made and equivalents may be substituted for elements or compositions thereof without departing from the true scope of the invention. Therefore, it is intended that this invention not be limited to a particular embodiment disclosed, but that the invention will include all embodiments falling within the scope of the appended claims.

We claim:

1. A composition comprising at least one steviol glycoside and a non-steviol glycoside composition, wherein the non-steviol glycoside composition is made by a process comprising the steps of:
   a. providing *Stevia rebaudiana* plant material;
   b. providing extraction solvent;
   c. mixing the *Stevia rebaudiana* plant material and the extraction solvent to provide a *Stevia* plant material and solvent mixture;
   d. separating the *Stevia* plant material and solvent mixture to obtain a filtrate comprising steviol glycoside molecules and non-steviol glycoside molecules; and
   e. isolating or separating the steviol glycoside molecules from the filtrate to obtain the non-steviol glycoside composition,
   wherein the obtained non-steviol glycoside composition comprises at least one non-steviol glycoside molecule selected from phenolic compounds, polyphenols, flavonoids, quinic and caffeic acids and their derivatives, neo-chlorogenic acid (neo-CGA; 5-O-caffeoylquinic acid or 5-CQA), crypto-chlorogenic acid (crypto-CGA; 4-O-caffeoylquinic acid or 4-CQA), n-chlorogenic acid (n-CGA; 3-O-caffeoylquinic acid or 3-CQA), iso-chlorogenic acid A (iso-CGA A; 3,5-dicaffeoylquinic acid) iso-chlorogenic acid B (iso-CGA B; 3,4-dicaffeoylquinic acid), iso-chlorogenic acid C (iso-CGA C; 4,5-dicaffeoylquinic acid), other chlorogenic acids and iso-chlorogenic acids known to art, retinoids, pigments, polysaccharides, olygosaccharides, disaccharides, monosaccharides, volatile oil components, sterols, terpenoids, sesquiterpenoids, diterpenes, triterpenes, coumarins, fatty acids and their derivatives, amino acids and their derivatives, dipeptides, oligopeptides, polypeptides, proteins, austroinulin, quercetin, sterebins, spathulenol, decanoic acid, 8,11,14-ecosatrienoic acid, 2-methyloctadecane, pentacosane, octacosane, stigmasterol, bsitosterol, a- and b-amyrine, lupeol, b-amyrin acetate, pentacyclic triterpene and/or glycosides thereof, and combinations thereof,
   wherein the at least one steviol glycoside is selected from the group consisting of rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, dulcoside A, dulcoside B, rubusoside, steviolmonoside, steviolbioside, stevioside, and combinations thereof, and
   wherein the non-steviol glycoside composition is a solubilizing agent, a flavor composition, a flavor modifier composition, a flavor enhancer composition, or a food ingredient.

2. A consumable comprising the composition of claim 1.

3. The consumable of claim 2, wherein the consumable is a food, beverage, pharmaceutical composition, tobacco product, nutraceutical product, oral hygienic composition, or cosmetic.

4. The composition of claim 1, wherein the at least one steviol glycoside comprises rebaudioside A.

5. The composition of claim 1, wherein the at least one steviol glycoside comprises rebaudioside D.

6. The composition of claim 1, wherein the at least one steviol glycoside comprises rebaudioside M.

* * * * *